US009631242B2

(12) United States Patent
Johnson et al.

(10) Patent No.: US 9,631,242 B2
(45) Date of Patent: Apr. 25, 2017

(54) METHOD FOR DETECTION OF VIABLE ENDOPHYTE IN PLANTS

(71) Applicant: GRASSLANZ TECHNOLOGY LIMITED, Palmerston North (NZ)

(72) Inventors: Richard David Johnson, Palmerston North (NZ); Christine Rosalie Voisey, Palmerston North (NZ)

(73) Assignee: GRASSLANZ TECHNOLOGY LIMITED, Hamilton (NZ)

( * ) Notice: Subject to any disclaimer, the term of this patent is extended or adjusted under 35 U.S.C. 154(b) by 482 days.

(21) Appl. No.: 14/351,601

(22) PCT Filed: Sep. 28, 2012

(86) PCT No.: PCT/NZ2012/000173
§ 371 (c)(1),
(2) Date: Jul. 1, 2014

(87) PCT Pub. No.: WO2013/077747
PCT Pub. Date: May 30, 2013

(65) Prior Publication Data
US 2014/0349302 A1 Nov. 27, 2014

Related U.S. Application Data

(60) Provisional application No. 61/548,438, filed on Oct. 18, 2011.

(51) Int. Cl.
*C12P 19/34* (2006.01)
*C12Q 1/68* (2006.01)
*G01N 33/569* (2006.01)

(52) U.S. Cl.
CPC ..... *C12Q 1/6895* (2013.01); *G01N 33/56961* (2013.01); *C12Q 2600/13* (2013.01); *C12Q 2600/156* (2013.01); *C12Q 2600/158* (2013.01)

(58) Field of Classification Search
USPC .................................................. 435/6.12, 91.2
See application file for complete search history.

(56) References Cited

U.S. PATENT DOCUMENTS

| | | | |
|---|---|---|---|
| 6,111,170 A | 8/2000 | Latch et al. | |
| 2003/0195117 A1 | 10/2003 | Imada et al. | |
| 2011/0182862 A1* | 7/2011 | Green | C12R 1/645 424/93.5 |

FOREIGN PATENT DOCUMENTS

| | | |
|---|---|---|
| JP | 2005-245287 | 9/2005 |
| NZ | 233083 | 12/1991 |

OTHER PUBLICATIONS

Belanger, F., A rapid seedling screening method for determination of fungal endophyte viability, Crop Science, 1996, 36(2): 460-462.
Fletcher, L.R., et. al., The impact of Acremonium endophytes in New Zealand, past, present and future, Proceedings of the New Zealand Grassland Association, 1990, 52: 227-235.
Fletcher, L,R., "Non-toxic" endophytes in ryegrass and their effects on livestock health and production, In Ryegrass endophyte: an essential New Zealand symbiosis, 1999.
Fletcher, L.R. et. al., Using Endophytes for pasture improvement in New Zealand, In Proceedings of the Grassland Conference 2000, 4th International Neotyphodium/Grass Interactions Symposium, Eds. Paul, V.H. et. al., Paderborn, pp. 149-162.
Ganley, A.R., etal.,Extraordinary ribosomal spacer length heterogeneity in a neotyphodium endophyte hybrid; implications for concerted evolution,Genetics,1998,150(4);1625-37.
Holder, T.L., et. al., Incidence and viability of Acremonium endophytes in tall fescue and meadow fescue plant introductions, Crop Science, 1994, 34(1):252-254.
Lacava, P.T., et. al., Rapid, specific and quantitative assays for the detection of the endophytic bacterium Methylobacterium mesophilicum in plants, J. Microbiol. Methods, 2006, 65(3): 535-41. Epub Nov. 2, 2005.
Leuchtmann, A., Ecological diversity in Neotyphodium-infected grasses as influenced by host and fungus characteristics, Neotyphodium/Grass Interactions, Eds. Bacon, C.W., et. al., Plenum Press, New York, 1997, pp. 93-103.
Newton, C.R., et. al., Analysis of any point mutation in DNA. The amplification refractory mutation system (ARMS), Nucleic Acids Research, 1989, 17(7):2503-2518.
Oliveira, J.A., et. al., Incidence and viability of Acremonium endophytes in tall fescue accessions from North Spain, Genetic Resources and Crop Evolution, 1997, 44(6): 519-522.
Rowan, D.D., et. al., Utilization of endophyte-infected perennial ryegrass for increased insect resistance, In Biotechnology of endophyte fungi in grasses, Eds. Bacon, C.W. et. al., CRC Press, 1994, pp. 169-183.
Stuedemann, J.A., et. al., Fescue endophyte: History and impact on animal agriculture, Journal of Production of Agriculture, 1988, 1: 39-44.

(Continued)

*Primary Examiner* — Kenneth Horlick
(74) *Attorney, Agent, or Firm* — Jondle & Associates, P.C.

(57) ABSTRACT

The invention provides a method and compositions for detecting the presence of viable endophyte in a plant, the method comprising germinating seed and excising a young leaf, optionally preparing an extract from the young leaf, and performing antibody, nucleic acid, or preferably PCR-based methods to detect the viable endophyte, wherein at least one primer hybridizes to the intergenic region (IGS) of the ribosomal repeat region of a specific endophyte when used in a PCR-based method. The invention provides a new method for rapid identification of both viable beneficial endophytes and any viable contaminating endophytes, as opposed to any non-viable endophytes, by detecting the presence of endophytes in the first leaf of germinated plants.

36 Claims, 4 Drawing Sheets

(56) References Cited

OTHER PUBLICATIONS

Welty, R.E., et. al., Detecting viable Acremonium endophytes in leaf sheaths and meristems of tall fescue and perennial ryegrass, Plant Dis, The American Phytopathological Society, 1986, 70: 431-435.

Wulff, E.G,, et. al., The ability of the biological control agent *Bacillus subtillis*, strain BB, to colonise vegetable brassicas endophytically following seed inoculation, Plant and Soil, 2003, 255: 463-474.

Zietkiewicz, E., et. al., Genome fingerprinting by simple sequence repeat (SSR)—anchored polymerase chain reaction amplification, Genomics, 1994, 20(2):176-83.

\* cited by examiner

Ribosomal Repeat gene

Figure 3

```
Ar1     GAAGAGTTACTAGCTGATGCGCTGTTGTTCTCTGTGTGGGCGCTGTTGT----------  49
AR42    GAAGAGTTACTAGCTGATGCGCTGTTGTTCTCTGTGTGGGCGCTGTTGTTCTCTGTGTGG  60
wild    GAAGAGTTACTAGCTGATGCNCTNNTGTTCTCTGTGTGGGCGCTGTTGTTCTCTGTGCGG  60
Ar37    GAAGAGTTACTAGCTGATGCGATGTTGTGCTCTGTGCGGGCGCTGTTGT----------  49
        ******************  *   *  **  **********

Ar1     ----------GCTCTGTGCGGGCGATGGTTCCTCTGTGCGGGCGCTGTCCTTGTGCGTGC  99
AR42    GCGCTGTTGTGCTCTGTGCGGGCGATGGTTCCTCTGTGCGGGCGCTGTCCTTGTGCGTGC 120
wild    GCGCTGTTGTGCTCTGTGCGGGCGATGGTTCCTCTGTGCGGGCGCTGTCCTTGTGCGTGC 120
Ar37    ----------GCTCTGTGCGGGCGATGGTTCCTTTGTGCGGGCGCTGTCCTTGTGCGTGC  99
                  *********************** ************************

Ar1     GTGCGATGTTGTTGTGTACGGGCGCGCTCATGTGCGGGCAGTGTAGGTTAGGCGCCTAAC 159
AR42    GTGCGATGTTGTTGTGTACGGGCGCGCTCATGTGCGGGCAGTGTAGGTTAGGCGCCTAAC 180
wild    GTGCGATGTTGTTGTGTACGGGCGCGCTCATGTGCGGGCAGTGTAGGTTAGGCGCCTAAC 180
Ar37    GTGCGATGTTGTTATGTACGGGCGCGCTCATGTGCGGGCAGTGTAGGTTAGGCGCCTAAC 159
        ********** * ********************************************

Ar1     CTATACCTGCCCGCGCACGCTGTGGGTGTGCGGGCGATGGTTCCTCTGTGCGGGCGCTGT 219
AR42    CTATACCTGCCCGCGCACGCTGTGGGTGTGCGGGCGATGGTTCCTCTGTGCGGGCGCTGT 240
wild    CTATACCTGCCCGCGCACGCTGTGGGTGTGCGGGCGATGGTTCCTCTGTGCGGGCGCTGT 240
Ar37    CTATACCTGCCCGCGCACGCTGTGGGTGTGCGGGCGATGGTTCCTCTGTGCGGGCGCTGT 219
        ************************************************************

Ar1     CCTTGTGCGTGCGGGCGATGTTATGCTCTGTGTGGGTGATGTTATCCTCTGTGCGGGCGC 279
AR42    CCTTGTGCGTGCGGGCGATGTTATGCTCTGTGTGGGTGATGTTATCCTCTGTGCGGGCGC 300
wild    CCTTGTGCGTGCGGGCGATGTTATGCTCTGTGTGGGTGATGTTATCCTCTGTGCGGGCGC 300
Ar37    CCTTGTGCGTGCGGGCGATGTTATGCTCTGTGTGGGTGATGTTATCCTCTGTGCGGGCGC 279
        ************************************************************

Ar1     TGTTGTCCTCTGTGGGTGATGCTGTCCTCTATGCAGGCGCTGTTGTCCTCTGTGCGAGCG 339
AR42    TGTTGTCCTCTGTGGGTGATGCTGTCCTCTATGCAGGCGCTGTTGTCCTCTGTGCGAGCG 360
wild    TGTTGTCCTCTGTGGGTGATGCTGTCCTCTATGCAGGCGCTGTTGTCCTCTGTGCGAGCG 360
Ar37    TGTCGTCCTCTGTG-------------------CGAGCGCTATTATTCTCCGTGTGGGCG 320
        *  *******                    *   ***   *  * *  *  ***

Ar1     CTAGTGTTCTCTATG----------------------CGGGTGATGTTATTCTCTGTG 375
AR42    CTAGTGTTCTCTATGTGGGTGATGTTATTATTCTCTATGCGGGTGATGTTATTCTCTGTG 420
wild    CTAGTGTTCTCTATGTGGGTGATGTTATTATTCTCTATGCGGGTGATGTTATTCTCTGTG 420
Ar37    CT------------------------------------------GTCGTCCTCTGTG 335
                                                    * *******

Ar1     CGAGCGCTATTATTCTCCGTGTGGGCGCTGTTATCCTCTATGTGGGCGCTGTGGGTGTGC 435
AR42    CGAGCGCTATTATTCTCCGTGTGGGCGCTGTTATCCTCTATGTGGGCGCTGTGGGTGTGC 480
wild    CGAGCGCTATTATTCTCCGTGTGGGCGCTGTTATCCTCTATGTGGGCGCTGTGNNTGTGC 480
Ar37    CGAGCGCTATTATTCTCCGTGTGGGCGCTGT--------------------GGGTGTGC 374
        *******************************                    *  ****

Ar1     GTGCGGGCAATGCTATTATATGTAGG 461
AR42    GTGCGGGCAATGCTATTATATGTAGG 506
wild    GTGCGGGCAATGCTATTATATGTAGG 506
Ar37    GTGCGGGCAATGCTATTATATGTAGG 400
        **************************
```

METHOD FOR DETECTION OF VIABLE ENDOPHYTE IN PLANTS

This application is the U.S. National Phase under 35 U.S.C. 371 of International Application PCT/NZ2012/000173, filed Sep. 8, 2012, and published in English, which claims the benefit of priority to U.S. Provisional Application No. 61/548,438, filed Oct. 18, 2011. The disclosure of each of the above-listed priority applications is incorporated herein by reference in its entirety.

TECHNICAL FIELD

The invention is in the field of pastoral agriculture. The invention relates to a method for detecting viable endophytes in grass plants.

BACKGROUND ART

Fungal endophytes infect a number of temperate climate grass species. Endophytes can produce alkaloids which are considered to confer degrees of pest and possibly disease protection upon the plants in which they naturally occur (Rowan and Latch, 1994). Furthermore, the presence of at least some endophytes may be essential for the competitive persistence of the chosen grass in a pasture (Fletcher and Easton, 2000).

However, many of the predominating natural endophyte infections of improved grass cultivars used for pastoral agriculture production also cause significant disorders in animals grazing on such grasses. Examples of such disorders include tall fescue toxicoses (Stuedemann and Hoveland, 1988) and ryegrass staggers (Fletcher et al., 1999). These conditions are the result of complex toxic reactions by animals to alkaloids produced under a range of plant growth conditions. Significant economic loss within pastoral agriculture systems can occur due to such animal toxicoses.

Grass lines can be artificially infected with selected beneficial endophytes that only produce desirable alkaloids. Axenic cultures of endophytes can be used to infect grass seedlings, grown initially under sterile conditions, which are then selected for desirable qualities, and multiplied for commercial use.

Three significant examples of this technology have been developed by the Grasslands division of AgResearch Ltd: GREENSTONE™ tetraploid hybrid ryegrass with ENDOSAFE™ endophyte (NZ Patent 233083); various perennial and hybrid ryegrasses with AR1 endophyte (Fletcher and Easton, 2000); and tall fescue cultivars with MaxQ® endophyte (U.S. Pat. No. 6,111,170).

When preparing seeds with beneficial endophyte strains for commercial production, it is possible for seed batches to contain other contaminating and potentially harmful endophyte strains. It is thus important to have means available to test the endophyte content (beneficial and/or non-beneficial) of such seeds batches and/or parental material. In addition it is important to know if any endophyte present is viable, that is able to grow with the plant to form a stable symbiosis.

Various methods have been developed to test plant tissues, and seed, for the presence of endophytes.

Some methods such as microscopy, with histological staining with compounds such as aniline blue, only detect the presence of endophytes, and do not identify easily or reliably identify the species or strain of endophyte. In addition, current approaches using microscopy do not distinguish between viable and non-viable endophytes.

Monoclonal antibody kits can be used to indicate at a gross level the type of endophyte present by determining what alkaloids are being produced. But such kits cannot determine the actual species or strain.

High Performance Liquid Chromatography (HPLC) can be used to quantify toxic alkaloids produced by endophytes, which can be correlated with endophyte strains present. However again, this method does not distinguish between viable and non-viable endophytes.

Nucleic acid methods, such as polymerase chain reaction (PCR), have been used to detect the presence of specific strains in grass seed and plant tissue, but current approaches lack sensitivity and require significant time to grow plants to a suitable stage of development before they can be tested for the presence of endophyte. Furthermore, current methods do not distinguish viable from non viable endophyte.

Isozymes can be used to profile endophytes but again this method does not distinguish between viable and non-viable endophytes.

The current industry standard method for detecting the presence of viable endophytes requires live endophyte to grow out of host plant tissue onto axenic media to confirm viability. Enzyme Linked Immunosorbant Assay (ELISA) is then typically used to determine the percentage of contamination based on alkaloid profile, and the Western blotting (protein immunoblot) analytical technique is used to determine the presence or absence of endophyte. This method is labour intensive and time consuming. Furthermore, such serological methods often cannot distinguish between endophyte strains that produce similar alkaloid profiles.

Thus, many of the currently available methods are time consuming and expensive. Some of the methods also lack sensitivity, and/or are not amenable to screening of multiple samples, with a quick turnaround time from seed to result. Furthermore, as discussed, many of such methods are unable to distinguish between the presence of viable and non-viable endophytes.

It is an object of the invention to provide a method for detecting the presence of viable endophyte in plants that overcomes one or more of the difficulties associated with the prior art, and/or at least to provide the public with a useful choice.

SUMMARY OF THE INVENTION

The applicants have invented a rapid method for detecting presence of viable endophytes in plants. Using the method of the invention it is possible to quickly identify plants containing viable endophytes, as opposed to those containing non-viable endophytes, by detecting the presence of endophytes in the first leaf of germinated plants. The method allows for early identification of both viable beneficial endophytes and any viable contaminating endophytes.

The method of the invention is amenable to testing (either manually or by automated processes) plant tissues, such as germinated seedlings from samples of seed batches, to determine the presence of particular viable beneficial and/or viable non-beneficial endophyte species and strains. The method can thus be used in quality control to determine the percentage of viable beneficial or viable contaminant endophytes, in seed batches for commercial production.

Method for Detection of Viable Endophyte

In the first aspect the invention provides a method for detecting the presence of viable endophyte in a plant, the method comprising detecting the presence of an endophyte in a young leaf or extract thereof, from the plant, wherein detecting the presence of the endophyte in the young leaf or extract is indicative of the presence of viable endophyte in the plant.

Young Leaf Defined by Leaf Number?

In one embodiment the young leaf is one of the first 5 leaves produced by the plant after germination of a seed of the plant. Preferably the young leaf is one of the first 4 leaves, more preferably the first 3 leaves, more preferably the first 2 leaves, produced by the plant after germination of a seed of the plant.

In a preferred embodiment the young leaf the first leaf produced by the plant after germination of a seed of the plant.

By using an early leaf, preferably the first leaf, as opposed to more mature plant tissue, it is possible to significantly reduce the time from germinating the seed to detecting viable endophyte. Thus the method of the invention is rapid, which is a significant benefit to the pastoral/seed industry.

Young Leaf Defined by Seedling Age?

In one embodiment the young leaf is a leaf from a seedling of the plant that is produced within 4 weeks, more preferably within 3 weeks, more preferably within 2 weeks, after germination of a seed of the plant.

In one embodiment the young leaf is from a seedling of the plant that is produced less than 14 days, preferably lest than 13 days, preferably lest than 12 days, preferably lest than 11 days, after germination of a seed of the plant.

In a preferred embodiment the young leaf is from a seedling of the plant that is produced about 10 days after germination of a seed of the plant. More preferably the young leaf is from a seedling of the plant that is produced 10 days after germination of a seed of the plant.

By using a young leaf, preferably from a seedling of the plant that is produced about 10 days after germination, as opposed to more mature plant tissue, it is possible to reduce the time from germinating the seed to detecting viable endophyte. Thus the method of the invention is rapid, which is a significant benefit to the pastoral/seed industry.

Young Leaf Defined by Development

Preferably the young leaf is from a seedling that has grown sufficiently for the leaf to have separated from the coleoptile.

Excising the Young Leaf

In one embodiment, the young leaf is excised, to substantially separate it from other tissues or organs of the plant, before use in the method.

In a further embodiment, the young leaf is excised, to substantially separate it from the coleoptile, as well as from other tissues or organs, of the plant, before use in the method.

In a further embodiment, the young leaf is excised, to substantially separate it from the coleoptile and any attached seed, as well as from other tissues or organs, of the plant, before use in the method.

Viable

The term "viable" as used herein means capable of growth. Preferably the "viable" endophyte is capable of growing within a plant to form a stable symbiosis.

Detecting the Presence of Viable Endophyte?

The applicants discovered that only viable endophyte (and not non-viable endophyte) can grow into the young leaf (particularly the first emerging leaf) of a germinating seedling, and shown that it is possible, using the method of the invention, to distinguish between plants containing viable endophyte and those not containing viable endophyte at the young leaf stage. Thus the applicant's invention relates to detecting the presence of viable endophyte. The method of the invention is sensitive enough to detect and identify viable endophyte in a young leaf when fungal biomass would typically be very low.

In one embodiment of the method of the endophyte is detected in the young leaf by any one of the following approaches: light microscopy, staining and light microscopy, electron microscopy, an antibody-based method, a monoclonal antibody-based method, enzyme-linked immunoassay (ELISA), high performance liquid chromatography (HPLC), nuclear magnetic resonance (NMR), near-infrared spectroscopy, an isozyme-based method, a nucleic acid-based method, a nucleic acid probe based method, a nucleic acid primer-based method, a PCR-based method.

Preferably the endophyte is detected by a method that identifies the presence of a particular species or strain of endophyte.

Preferred methods for detecting the presence of a particular species or strain of endophyte include the following: antibody-based methods, monoclonal antibody-based methods, enzyme-linked immunoassay (ELISA), nucleic acid-based methods, nucleic acid probe-based methods, nucleic acid primer-based methods, and PCR-based methods.

In a preferred embodiment the endophyte is detected by a nucleic acid based method.

In a preferred embodiment the endophyte is detected by a PCR-based method. In one embodiment the PCR-based method is quantitative PCR. In a preferred embodiment the PCR-based method is real time PCR In a more preferred embodiment the PCR-based method is High Resolution Melting (HRM) real time PCR PCR Primers Used in the Method In one embodiment PCR is performed using primers that hybridise to nucleic acid in the endophyte.

In a preferred embodiment the primers hybridise to a multi-copy number gene in the endophyte.

In a more preferred embodiment the primers hybridise to the intergenic region (IGS) of the ribosomal repeat region of the endophyte.

Specificity of Detection

In a preferred embodiment the detection is specific for a particular species or strain of the endophyte.

In one embodiment the primers used in the PCR-based method, are specific for the strain detected. In this embodiment presence or absence of an amplification product is indicative of presence or absence of the endophyte.

Alternatively specificity may be determined by the nature of amplified product. In one embodiment specificity is be determined by the size of the amplified product. In this embodiment products of a different size may be produced from different endophyte species or strains, using the same primers for amplification.

Alternatively specificity may be determined by the kinetics of production of amplified product. In one embodiment specificity is be determined by the melting profile. In this embodiment a different melting profiles may be produced from different species or endophyte strains, using the same primers from amplification.

The different melting profiles may be produced as a result of differences, such as single nucleotide polymorphisms (SNPs), insertions, deletions, and the like, found in sequences to which the prier hybridizes, in different endophyte species or strains.

Germination of Seed

Before use in the basic method of the invention, a seed of the plant is germinated.

Preferably the seed is germinated under conditions to maximize hyphal biomass in the young leaves.

Preferably the seed is germinated under conditions to maximize hyphal biomass in the seed in the first emerging leaf.

In one embodiment the seed are germinated in the temperature range 18 to 26° C. Preferably the seed are germinated in the temperature range 19 to 25° C., more preferably 20 to 24° C., more preferably 21 to 23° C. Most preferably seed are germinated at about 22° C.

In one embodiment the seed is germinated in a 16/8 hour light/dark regime. Preferably the seed is germinated in a 14/10 hour light/dark regime. More preferably the seed is germinated in about a 12/12 hour light/dark regime. Most preferably the seed is germinated in a 12/12 hour light/dark regime.

Preparing Extract from Young Leaf

Presence of the endophyte may be detected in an extract from the young leaf.

Method of the Invention Including the Step Preparing an Extract from the Young Leaf of the Plant In one embodiment of the invention the method includes the step of preparing an extract from the young leaf.

Thus, in one embodiment the invention provides a method for detecting the presence of viable endophyte in a plant, the method comprising the steps:
a) providing a young leaf,
b) preparing an extract from the young leaf, and
c) detecting the presence of an endophyte in the extract, wherein detecting the presence of the endophyte in the extract is indicative of the presence of viable endophyte in the plant.

Method of the Invention Including the Step of Excising the Young Leaf from the Plant Before Detecting the Endophyte In one embodiment of the invention the method includes the step of excising the young leaf.

Thus, in one embodiment the invention provides a method for detecting the presence of viable endophyte in a grass plant, the method comprising the steps:
a) providing a plant,
b) excising a young leaf, and
c) detecting the presence of an endophyte in the young leaf, wherein detecting the presence of the endophyte in the young leaf is indicative of the presence of viable endophyte in the plant.

Method of the Invention Including the Step of Excising the Young Leaf from the Plant, and Making an Extract from the Young Leaf, Before Detecting the Endophyte In one embodiment of the invention the method includes the steps of excising the young leaf and making an extract.

Thus, in one embodiment the invention provides a method for detecting the presence of viable endophyte in a plant, the method comprising the steps:
a) providing a plant,
b) excising a young leaf,
c) making an extract from the young leaf, and
c) detecting the presence of an endophyte in the extract, wherein detecting the presence of the endophyte in the extract is indicative of the presence of viable endophyte in the plant.

Method of the Invention Including the Step of Germinating the Seed and Excising the Young Leaf Before Detecting the Endophyte In one embodiment of the invention the method includes the steps of germinating the seed, and excising the young leaf.

Thus, in one embodiment the invention provides a method for detecting the presence of viable endophyte in a plant, the method comprising the steps:

a) germinating a seed and growing a plant until at least one young leaf is produced,
b) excising a young leaf from the plant, and
c) detecting the presence of an endophyte in a young leaf, wherein detecting the presence of the endophyte in the young leaf is indicative of the presence of viable endophyte in the plant.

Method of the Invention Including the Steps of Germinating the Seed, Excising the Young Leaf, and Making an Extract Before Detecting the Endophyte In one aspect of the invention the method includes the steps of germinating the seeds, excising the young leaf, and making an extract Thus, in one aspect the invention provides a method for detecting the presence of viable endophyte in a grass plant, the method comprising the steps:
a) germinating a seed and growing a plant until at least one young leaf is produced,
b) excising a young leaf from the plant,
c) making an extract from the young leaf, and
d) detecting the presence of an endophyte in the young leaf, wherein detecting the presence of the endophyte in the extract is indicative of the presence of viable endophyte in the grass plant.

Use of the Method for Screening Batches of Seed

The method of the invention may be used to screen batches of seed to assess which endophyte species, strain, or strains, are present.

For this approach, typically a small sample of seeds (for example 50 to 100 seeds) will be taken from the larger batch. The method will then be performed on a young leaves, as described herein, after germination of the seeds from the small sample.

The method of the invention may thus be used to measure the proportion or percentage of seeds in the small sample that contain viable endophytes of a particular species or strain, in order to estimate the proportion or percentage of seeds in the large batch that contain the viable endophytes.

The method of the invention may also be used to measure the proportion or percentage of seeds in the small sample that contain viable contaminating endophytes, in order to estimate the proportion or percentage of seeds in the large batch that contain viable contaminating endophytes.

Automated Embodiments

The method of the invention is amenable to automated processes. Any one of the steps may be automated. Steps that are particularly amenable to automated processes include the process of preparing an extract, and the detection stage, particularly the PCR-based stage.

In one embodiment at least one of these stages is automated. In a further embodiment both of these stages are automated.

Plants

The term "plant" includes seeds and seedlings as well as more mature plants. The "plant" provided for use in the method may therefore be a seedling.

Furthermore, the method of the invention for detecting the presence of viable endophyte in a plant can also be considered to be for detecting the presence of viable endophyte in the seed from which the plant was produced. As discussed herein, the method can be applied to batches of seed and to assessing the proportion or percentage of viable endophytes in such seed batches by performing the method of a sample of such seed after germination of such seed.

Source of Plants

The plant may be from any species capable of forming stable symbiosis with the endophyte.

In one embodiment the plant is from a dicotyledonous species.

In a preferred embodiment the plant is from a monocotyledonous species.

Preferred monocotyledonous genera include: *Agropyron, Allium, Alopecurus, Andropogon, Arrhenatherum, Asparagus, Avena, Bambusa, Bellavalia, Thimeura, Brodiaea, Bulbocodium, Bothrichloa, Bouteloua, Bromus, Calamovilfa, Camassia, Cenchrus, Chionodoxa, Chloris, Colchicum, Crocus, Cymbopogon, Cynodon, Cypripedium, Dactylis, Dichanthium, Digitaria, Elaeis, Eleusine, Eragrostis, Eremurus, Erythronium, Fagopyrum, Festuca, Fritillaria, Galanthus, Helianthus, Hordeum, Hyacinthus, Hyacinthoides, Ipheion, Iris, Leucojum, Liatris, Lolium, Lycoris, Miscanthis, Miscanthus×giganteus, Muscari, Ornithogalum, Oryza, Panicum, Paspalum, Pennisetum, Phalath, Phleum, Poa, Puschkinia, Saccharum, Secale, Setaria, Sorghastrum, Sorghum, Thinopyrum, Triticum, Vanilla,* X *Triticosecale Triticale* and *Zea*.

Preferred monocotyledonous species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Allium fistulosum, Allium sativum, Alopecurus pratensis, Andropogon gerardi, Andropogon Gerardii, Andropogon scoparious, Arrhenatherum elatius, Asparagus officinalis, Arena nuda, Arena sativa, Bambusa vulgaris, Bellavalia trifoliate, Brimeura amethystina, Brodiaea californica, Brodiaea coronaria, Brodiaea elegans, Bulbococlium versicolor, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Camassia scilloides, Cenchrus ciliaris, Chionodoxa forbesii, Chloris gayana, Colchicum autumnale, Crocus sativus, Cymbopogon nardus, Cynodon dactylon, Cypripedium acaule, Dactylis glomerata, Dichanthium annulatum, Dichanthium aristatum, Dichanthium sericeum, Digitaria decumbens, Digitaria smutsii, Elaeis guineensis, Elaeis oleifera, Eleusine coracan, Elymus angustus, Elymus junceus, Eragrostis curvula, Eragrostis tef, Eremurus robustus, Erythronium elegans, Erythronium helenae, Fagopyrum esculentum, Fagopyrum tataricum, Festuca arundinacea, Festuca ovina, Festuca pratensis, Festuca rubra, Fritillaria cirrhosa, Galanthus nivalis, Helianthus annuus* sunflower, *Hordeum distichum, Hordeum vulgare, Hyacinthus orientalis, Hyacinthoides hispanica, Hyacinthoides non-scripta, Ipheion sessile, Iris collettii, Iris danfordiae, Iris reticulate, Leucojum aestivum, Liatris cylindracea, Liatris elegans, Lolium arundinaceum, Lolium longiflorum, Lolium multiflorum, Lolium perenne, Lolium westerwoldicum, Lolium hybridum, Lycoris radiata, Miscanthis sinensis, Miscanthus×giganteus, Muscari armeniacum, Muscari macrocarpum, Narcissus pseudonarcissus, Ornithogalum montanum, Oryza sativa, Panicum italicium, Panicum maximum, Panicum miliaceum, Panicum purpurascens, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa nemoralis, Puschkinia scilloides, Saccharum officinarum, Saccharum robustum, Saccharum sinense, Saccharum spontaneum, Scilla autumnalis, Scilla peruviana, Secale cereale, Setaria italica, Setaria sphacelata, Sorghastrum nutans, Sorghum bicolor, Sorghum dochna, Sorghum halepense, Sorghum sudanense, Thinopyrum ponticum, Trillium grandiflorum, Triticum aestivum, Triticum dicoccum, Triticum durum, Triticum monococcum, Tulipa batalinii, Tulipa clusiana, Tulipa dasystemon, Tulipa gesneriana, Tulipa greigii, Tulipa kaufinanniana, Tulipa sylvestris, Tulipa turkestanica, Vanilla fragrans,* X *Triticosecale* and *Zea mays*.

Certain preferred monocotyledonous plants include those from monocotyledonous forage species including but not limited to triticale, barley, wheat, sorghum and maize.

Particularly preferred monocotyledonous plants include grasses. Preferred grasses include those from the Poaceae family. Preferred Poaceae grasses include perennial ryegrass (*Lolium perenne*), Italian ryegrass (*Lolium multiflorum*), cocksfoot (*Dactylis glomerata*), and tall fescue (*Festuca arundinacea* syn *Lolium arundinaceum*).

Other preferred grasses include those of the subfamily pooideae. Preferred pooideae plants include wheat, barley, oats, brome grass and reed grass.

Other preferred grasses include those of the subfamily panicoideae. Preferred panicoideae plants include panic grass, maize, sorghum, sugar cane, millet, fonio and bluestem grasses.

Particularly preferred grass species include *Lolium longiflorum, Lolium multiflorum, Lolium perenne, Lolium westerwoldicum, Lolium hybridism, Festuca arundinacea* syn *Lolium arundinaceum, Festuca ovina, Festuca pratensis, Festuca rubra,* and *Zea mays*.

In one embodiment the grass is from the genus *Lolium*. Preferred *Lolium* species include *Lolium arundinaceum Lolium longiflorum, Lolium multiflorum, Lolium perenne, Lolium westerwoldicum, Lolium hybridum*. A particularly preferred *Lolium* species is *Lolium perenne*.

In a further embodiment the grass is from the genus *Festuca*. Preferred *Festuca* species include *Festuca arundinacea, Festuca ovina, Festuca pratensis, Festuca rubra*. A particularly preferred *Festuca* species is *Festuca arundinacea* syn *Lolium arundinaceum*.

*Lolium arundinaceum* is a synonym to *Festuca arundinacea*. And the two names can be used interchangeably Endophyte The endophyte may be from any species capable of forming stable symbiosis with the plant.

Preferably the endophyte is a fungal endophyte from the division Ascomycota. Preferably the endophyte is a fungal endophyte from the family Clavicipitaceae.

Preferably the endophyte is selected from the genera *Neotyphodium* or *Epichloë*.

In one embodiment the endophyte is from the genus *Neotyphodium*.

Preferred *Neotyphodium* species include: *Neotyphodium aotearoae, Neotyphodium australiense, Neotyphodium chilense, Neotyphodium chisosum, Neotyphodium coenophialum, Neotyphodium gansuense, Neotyphodium buerfanum, Neotyphodium lolii, Neotyphodium melicicola, Neotyphodium occultans, Neotyphodium siegelii, Neotyphodium starrii, Neotyphodium tembladerae, Neotyphodium typhinum, Neotyphodium uncinatum, Neotyphodium sinicum* and *Neotyphodium sinofestucae*.

A particularly preferred *Neotyphodium* species is *Neotyphodium lolii*.

Particularly preferred *Neotyphodium lolii* strains include AR1, AR5, AR6 and AR37.

A particularly preferred *Neotyphodium lolii* is AR1.

Another particularly preferred *Neotyphodium lolii* is AR37.

Another particularly preferred *Neotyphodium* species is *Neotyphodium coenophialum*.

Particularly preferred *Neotyphodium coenophialum* strains include AR542, AR584 and AR601.

Another particularly preferred *Neotyphodium coenophialum* strain is AR542.

In another embodiment the endophyte is from the genus *Epichloë*:

Preferred *Epichloë* species include: *Epichloë bromicola*, *Epichloë festucae* and *Epichloë sylvatica*.

A particularly preferred *Epichloë* species is *Epichloë festucae*.

A preferred *Epichloë festucae* strain is AR1501.

Other preferred endophytes include P-endophytes. Preferred P-endophytes include *Gliocladium*-like and *Phialophora*-like endophytes.

Endophyte Deposits

The terms AR1, AR5, AR6, AR37, AR42, AR542, AR584, AR601 and AR1501 refer to endophyte strains that can be distinguished from other endophytes by their genotype, e.g. microsatellite pattern. These following endophyte strains have been deposited at the National Measurement Institute (NMI), Suakin Street, Pymble, New South Wales, Australia according to the Budapest Treaty for purposes of patent procedure.

| Strain | Species | Depository | Deposit date | Deposit Number |
|---|---|---|---|---|
| AR1 | *N. lolii* | NMI | 12 May 1998 | NM98/04669 |
| AR5 | *N. lolii* | NMI | 23 Jul. 2007 | VO7/029055 |
| AR6 | *Neotyphodium* sp. (LpTG-2) | NMI | 14 Oct. 2008 | V08/0211261 |
| AR37 | *N. lolii* | NMI | 23 May 2003 | NM03/35819 |
| AR542 | *N. coenophialum* | NMI | 12 May 1998 | NM02/04675 |
| AR584 | *N. coenophialum* | NMI | 12 May 1998 | NM02/04676 |
| AR601 | *N. coenophialum* | NMI | 23 Jul. 2007 | V07/029058 |

PCR Primers

In a further aspect the invention provides a primer that hybridises to the intergenic region (IGS) of the ribosomal repeat region of the endophyte.

In one embodiment the primer hybridises to species-specific or strain-specific region of the intergenic region (IGS) of the ribosomal repeat region of the endophyte.

Preferably the endophyte is an endophyte as described herein.

In one embodiment the primer has at least 70% identity to any one of the sequences of SEQ ID NO:1 to SEQ ID NO:8.

In a further embodiment the primer has the sequences of any one of SEQ ID NO:1 to SEQ ID NO:8.

In one embodiment of the method of the invention the endophyte is detected by a PCR-based method using at least one primer of the invention. Preferably at least two primers of the invention are used in the method.

DETAILED DESCRIPTION

The applicants were aware that endophytes grow by intercalary extension in plants. The applicants discovered that only viable endophyte (and not non-viable endophyte) is found in the young leaf (particularly the first emerging leaf) of a germinating seedling or plant. The applicant's invention relates to detecting the presence of viable endophyte. Using the method of the invention, the applicants have shown that it possible to distinguish between plants that contain viable endophyte and those that contains no endophyte or only non-viable endophyte more quickly than in previous methods. The method of the invention is sensitive enough to detect and identify endophyte in a young leaf when fungal biomass would typically be very low.

Seeds often contain both viable and non-viable endophytes, but current approaches for distinguishing between seeds containing viable and those not containing endophyte or containing only non-viable endophyte are cumbersome and time consuming. Prior to the present invention the standard approach for detecting viable endophyte required live endophyte to grow out of host tissue pieces into axenic media to confirm endophyte viability. Such grow-out tests may also require microscopic detection of endophyte in advance of the grow-out stage.

The present invention thus provides a fast, convenient and cost effective alternative that is also amenable to automation.

Detecting the Presence of Viable Endophyte?

Antibody Based Methods

Antibodies may be used to detect the presence of endophytes in young leaves in the method of the invention. General methods for using antibodies as diagnostic tools are known in the art (Immunoassays: A Practical Approach, Gosling J. P. (Ed) Oxford University Press. Enzyme-linked immunosorbent assay (ELISA) monoclonal antibody and immunoblot approaches may be applied to the method of the invention.

For diagnostic detection of endophytes, antibodies may be specific for raised against whole cell extracts of fungal mycelium. Other antibodies that are available are those that detect endophyte alkaloids such as peramine, paxilline and lolines.

Nucleic Acid Based Methods

Diagnostic nucleic acid based methods are well known to those skilled in the art. Useful methods include probe-hybridization methods, and PCR-based methods.

Probe-Based Methods

Probe-based methods may be applied to detect the viable endophyte in the method of the invention. Methods for hybridizing probes to target nucleic acid sequences are well known to those skilled in the art (Sambrook et al., Eds, 1987, Molecular Cloning, A Laboratory Manual, 2nd Ed. Cold Spring Harbor Press).

The term "probe" refers to a short polynucleotide that is used to detect a polynucleotide sequence that is at least partially complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably at least 500 nucleotides in length.

The probe need not be completely complementary to the target DNA sequence. Differences between in the target sequence in different species or strains may be used to distinguish between species or strains when using the same probe.

PCR-Based Methods

PCR-based methods are particularly preferred for detection of endophyte in the method of the invention.

General PCR approaches are well known to those skilled in the art (Mullis et al., 1994). Various other developments of the basic PCR approach may also be advantageous applied to the method of the invention. Examples are discussed briefly below.

Allele Specific PCR

Allele-specific PCR is a diagnostic or cloning technique based on single-nucleotide polymorphisms (SNPs) (singlebase differences in DNA). It requires prior knowledge of a DNA sequence, including differences between alleles, and uses primers whose 3' ends encompass the SNP. PCR amplification under stringent conditions is much less efficient in the presence of a mismatch between template and primer, so successful amplification with an SNP-specific primer signals presence of the specific SNP in a sequence. (Newton et al., 1989)

Intersequence-Specific PCR

Intersequence-specific PCR (ISSR) is a PCR method for DNA fingerprinting that amplifies regions between simple sequence repeats to produce a unique fingerprint of amplified fragment lengths. (Zietkiewicz et al., 1994)

Multiplex-PCR

Multiplex-PCR utilises multiple primer sets within a single PCR reaction to produce amplified products (amplicons) of varying sizes that are specific to different target DNA sequences. By targeting multiple sequences at once, diagnostic information may be gained from a single reaction that otherwise would require several times the reagents and more time to perform. Annealing temperatures and primer sets are generally optimized to work within a single reaction, and produce different amplicon sizes. That is, the amplicons should form distinct bands when visualized by gel electrophoresis. Multiplex PCR can be used in the method of the invention to detect the presence of more than one endophyte in a single sample or reaction.

Quantitative PCR

Quantitative PCR (Q-PCR) is used to measure the quantity of a PCR product (commonly in real-time). Q-PCR quantitatively measures starting amounts of DNA, cDNA, or RNA. Q-PCR is commonly used to determine whether a DNA sequence is present in a sample and the number of its copies in the sample. Quantitative real-time PCR has a very high degree of precision. Q-PCR methods use fluorescent dyes, such as Sybr Green, EvaGreen or fluorophore-containing DNA probes, such as TaqMan, to measure the amount of amplified product in real time. Q-PCR is sometimes abbreviated to RT-PCR (Real Time PCR) or RQ-PCR. QRT-PCR or RTQ-PCR.

High Resolution Melt (HRM) Real-Time PCR

High Resolution Melt (HRM) analysis is a powerful technique for the detection of mutations, polymorphisms and epigenetic differences in double-stranded DNA samples. HRM analysis is performed on double stranded DNA samples. Typically the user will use polymerase chain reaction (PCR) prior to HRM analysis to amplify the DNA region in which their mutation of interest lies. This region that is amplified is known as the amplicon. After the PCR process the HRM analysis begins. The process is simply a precise warming of the amplicon DNA from around 50° C. up to around 95° C. At some point during this process, the melting temperature of the amplicon is reached and the two strands of DNA separate or "melt" apart. Differences between the melting profiles can be used in the method of the invention to distinguish between endophyte strains present.

Genotyping

It is possible to identify insertions or deletions (depending on the endophyte strain) that can be used to distinguish between different endophyte strains. PCR primers can be designed that they flank the insertion or deletion (or multiples of these) and produce specific amplicons of different sizes that can be separated by conventional gel electrophoresis or using a Genotyper (Life Technologies/Applied Biosystems) which identifies different sized peaks, to provide the genotype of the endophyte strain.

PCR Primers

The term "primer" refers to a short polynucleotide, usually having a free 3'OH group, that is hybridized to a template and used for priming polymerization of a polynucleotide complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

Preferably PCR is performed using primers that hybridise to nucleic acid in the endophyte.

The applicants have shown that it is possible to increase the sensitivity of detection by using primers hybridise to a multi-copy number gene, rather than a single copy gene, in the endophyte. Thus in a preferred embodiment the primers hybridise to a multi-copy number gene in the endophyte.

With such primers the applicants have successfully amplified endophyte DNA, thus detecting the presence of viable endophyte, in the young leaves of plants. At this developmental stage endophyte biomass is typically low, and difficult to detect via standard PCR or other methods.

The applicants identified the intergenic region (IGS) of the ribosomal repeat region for various endophytes, and showed that these regions can be targeted for PCR primer binding to provide a sensitive method for detection of endophyte.

Ribosomal ribonucleic acid (rRNA) is the RNA component of the ribosome. The ribosomal RNAs form two subunits (Figure), the large subunit (LSU) and small subunit (SSU). The 18S rRNA in most eukaryotes is in the small ribosomal subunit, and the large subunit contains three rRNA species (the 5S, 5.8S and 28S rRNAs). The 28S, 5.8S, and 18S rRNAs are encoded by a single transcription unit separated by 2 internally transcribed spacers (ITS). Each transcriptional unit is separated by an intergenic sequence (IGS). Eukaryotes generally have many copies of the rRNA genes organized in tandem repeats so there are multiple copies of both the genes and the IGS sequences. In fungi the 5S rRNA is typically encoded elsewhere in the genome so there is one larger IGS region as opposed to two smaller ones separated by the 5S gene (FIG. 2).

In a preferred embodiment the primers hybridise to the intergenic region (IGS) of the ribosomal repeat region of the endophyte.

In one embodiment the intergenic region (IGS) of the ribosomal repeat region of the endophyte comprises the sequence with at least 70% to part of the sequence of any one of SEQ ID NO: 9 to 16.

In one embodiment the intergenic region (IGS) of the ribosomal repeat region of the endophyte comprises the sequence of any one of SEQ ID NO: 9 to 16.

In a further embodiment primer has at least 70% to part of the sequence of any one of SEQ ID NO: 9 to 16.

In a one embodiment of the invention the primers used in the method have at least 70% identity to any one of the sequences of SEQ ID NO:1 to SEQ ID NO:8.

In a further embodiment the primer has the sequences of any one of SEQ ID NO:1 to SEQ ID NO:8.

Percent Identity

Variant polynucleotide sequences preferably exhibit at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 10 nucleotide positions, more preferably at least 10 nucleotide positions, more preferably at least 12 nucleotide positions, more preferably at least 13 nucleotide positions, more preferably at least 14 nucleotide positions, more preferably at least 15 nucleotide positions, more preferably at least 16 nucleotide positions, more preferably at least 17 nucleotide positions, more preferably at least 18 nucleotide positions, more preferably at least 19 nucleotide positions, more preferably at least 20 nucleotide positions, more preferably at least 21 nucleotide positions and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences may be examined using the following unix command line parameters:
bl2seq -i nucleotideseq1 -j nucleotideseq2 -F F -p blastn The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively the GAP program, which computes an optimal global alignment of two sequences without penalizing terminal gaps, may be used to calculate sequence identity. GAP is described in the following paper: Huang, X. (1994) On Global Sequence Alignment. Computer Applications in the Biosciences 10, 227-235.

Sequence identity may also be calculated by aligning sequences to be compared using Vector NTI version 9.0, which uses a Clustal W algorithm (Thompson et al., 1994, Nucleic Acids Research 24, 4876-4882), then calculating the percentage sequence identity between the aligned sequences using Vector NTI version 9.0 (Sep. 2, 2003 ©1994-2003 InforMax, licensed to Invitrogen).

Viable

The term "viable" as used herein with respect to endophytes means capable of growth. Preferably the "viable" endophyte is capable of growing within a plant to form a stable symbiosis.

Germination of Seed

Those skilled in the art will be well aware of materials and methods for germination seeds. The applicants have optimized seed germination conditions to maximize endophyte biomass in young leaves.

Thus in one embodiment the seed is germinated in the temperature range 18 to 26° C. Preferably the seed is germinated in the temperature range 19 to 25° C., more preferably 20 to 24° C., more preferably 21 to 23° C. Most preferably seed is germinated at about 22° C.

In a further embodiment the seed is germinated in a 16/8 hour light/dark regime. Preferably the seed is germinated in a 14/10 hour light/dark regime. More preferably the seed is germinated in about a 12/12 hour light/dark regime. Most preferably the seed is germinated in a 12/12 hour light/dark regime.

Excising a Young Leaf

In a preferred embodiment of the invention a young leaf is excised from the seedling or plant prior to detection of endophyte. Skilled workers will be aware of how to excise plant tissues and organs. Preferably excision should be performed aseptically to minimize contamination between different seedlings or plants.

Preferably, the young leaf is excised, to substantially separate it from other tissues or organs of the plant, before use in the method. More preferably, the young leaf is excised, to substantially separate it from the coleoptile, as well as from other tissues or organs, of the plant, before use in the method. Most preferably, the young leaf is excised, to substantially separate it from the coleoptile and any attached seed, as well as from other tissues or organs, of the plant, before use in the method.

The applicants have shown that such other tissues and organs (particularly seed coats and coleoptiles can harbor non-viable endophyte, which interferes with the method of the invention for detecting viable endophyte. Thus such other tissues should preferably be removed.

Coleoptile

The coleoptile is the pointed tubular protective sheath covering the emerging shoot in germinating monocotyledonous plants.

Young Leaf

A major advantage of the present invention is detection of the presence of viable endophyte (as opposed to non-viable endophyte) at an early stage of plant development. Thus the present method is quicker than other known methods of detecting viable endophytes in plants.

In order to make the time from germinating seed to detecting viable endophyte as short as possible, endophyte is preferably detected in the first leaf.

Although not preferred, older young leaves can also be used in the method of the invention.

In one embodiment the young leaf is one of the first 5 leaves produced by the plant after germination of a seed of the plant. Preferably the young leaf is one of the first 4 leaves, more preferably the first 3 leaves, more preferably the first 2 leaves, produced by the plant after germination of a seed of the plant.

In a preferred embodiment the young leaf the first leaf produced by the plant after germination of a seed of the plant.

First Leaf

The first leaf of a monocotyledonous plant is also called referred to as a cotyledon, a seed leaf, embryonic leaf or the first emerging leaf. All of these are encompassed by the term "first leaf" as used herein.

The applicants have shown that only viable endophyte can grow out of the meristem into first leaf primordia and subsequent young leaves. The first leaf primordium is also included within the term "first leaf" as used herein.

Preparing Extract from Young Leaf

The method of the invention optionally includes a step of producing an extract from the young leaf, before detection of the endophyte in the young leaf. The extraction procedure will of course depend on the technique used to detect the presence of the endophyte in the extract.

For antibody-based methods a protein extraction procedure is used. Several methods for preparing protein extracts from plants are known to those skilled in the art (REFS).

For nucleic based methods a nucleic acid extraction procedure is used. Several methods for preparing nucleic acid extracts from plants are known to those skilled in the art (see Protocol Online available on the world wide web www.protocol-online.org/biology-forums/DNA.html). Preferred nucleic acid extraction methods include DNA extraction methods.

Preferred DNA extraction methods include the Post method (Post et al., 2003. Euphytica 130: 255-260), and the HotShot method (see Protocol Online available on the World Wide Web www.protocol-online.org/biology-forums/DNA.html), the Genaid Genomic DNA Mini Kit—Plant (Geneaid Biotech Ltd). A particularly preferred DNA extraction method is the HotShot method.

The DNA extraction procedure may be advantageously automated in the method of the invention. DNA extraction procedures amenable to automation are well known to those skilled in the art. Automation may be via use of a robot (for example, Slipstream Automation, Palmerston North, New Zealand).

BRIEF DESCRIPTION OF THE DRAWINGS

FIG. 3 shows a DNA multiple sequence alignment using ClustalW for the IGS sequences obtained from AR1, AR37, AR42 and common toxic wild type *N. lolii* with primers RJ243F (IGSF, LR12R) and RJ243R (IGSR, invSRIR) (SEQ ID NO: 17 and 18). Nucleotide polymorphisms and insertions and deletions between strains are shown.

EXAMPLES

Example 1

Figure 1:
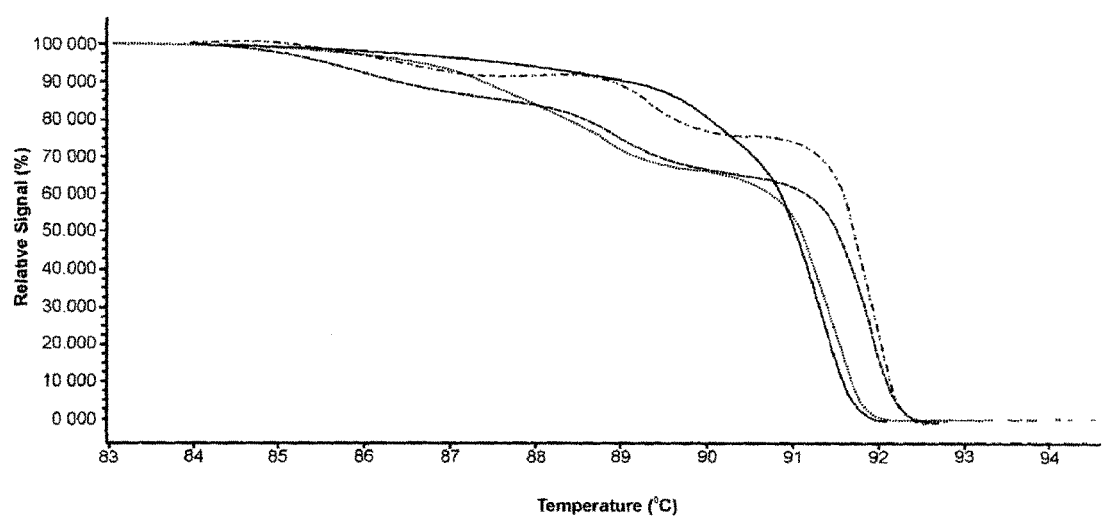
FIG. 1 shows High Resolution Melting (HRM) curves for different endophyte strains showing unique melting profiles. The HRM curve for AR1 is shown with a dotted line (··········). The HRM curve for AR37 is shown with a solid line (————). The HRM curve for the common toxic wild type *N. lolii* is shown with a dashed line (- - - - - - -). The HRM curve for AR42 is shown with a dot/dashed line (-·-·-·-).
Figure 2:
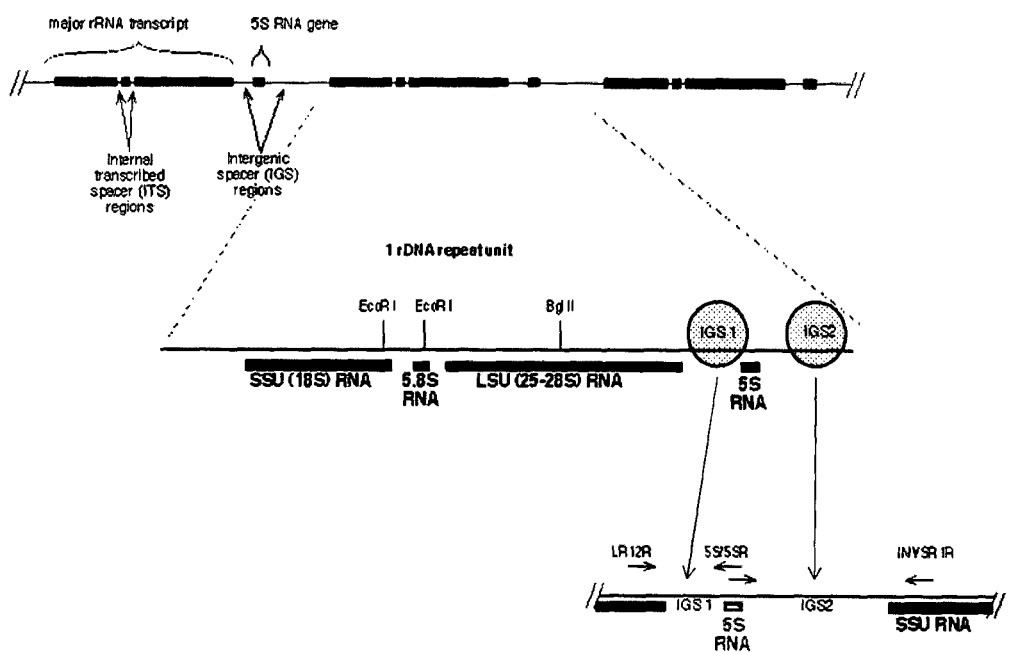
FIG. 2 shows generic ribosomal repeat structure from eukaryotes showing small (SSU) and large (LSU) subunit ribosomal RNAs and the internal transcribed spacer (ITS) and intergenic regions (IGS).
Figure 4:
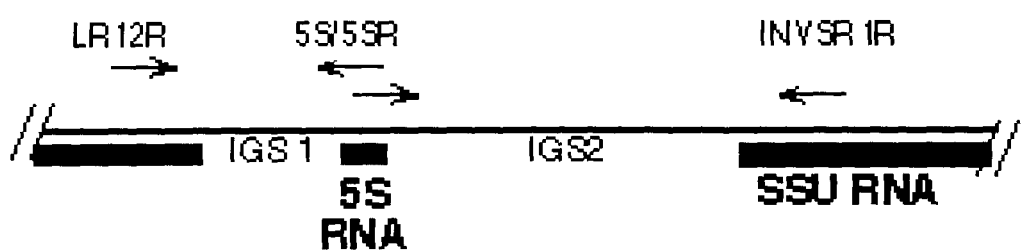
FIG. 4 shows the universal PCR primers for the Intergenic spacer sequence (IGS) used to amplify this region from different endophytes.

Identifying Endophyte Strain Specific Sequences as Targets for PCR Amplification Materials and Methods The universal primers (below) were synthesized based on IGS sequences (see Figure) from Duke University (available on the world wide web at http://www.biology.duke.edu/fungi/mycolab/primers.htm).

```
                                              (SEQ ID NO: 17)
RJ243F (IGSF, LR12R) GAACGCCTCTAAGTCAGAAATCC (SEQ ID NO: 18)
RJ243R (IGSR, invSRIR) ACTGGCAGAATCAACCAGGTA
```

PCR was performed on genomic DNA extracted from the following endophyte strains:
Common toxic wild type
AR1
AR42 (similar to wild type strain)
Common toxic wild type *N. lolii*
AR37
AR542
AR584
AR601
FL1
*E. ciliarus*

PCR reactions and cycling conditions were:

| | |
|---|---|
| 20 ul | reaction mix using 5 prime PCR Extender Kit |
| 2 ul | 10× Tuning Buffer |
| 0.4 ul | 25 mM dNTP's |
| 0.8 ul | 10 uM Primers (each) |
| 0.2 ul | 5 U/ul PCR Extender polymerase |
| | MQ up to 20 ul total volume |
| 40 ng | genomic DNA as template |

PCR Cycling Conditions

| | | |
|---|---|---|
| 93' C. | 3 min | |
| 93' C. | 15 sec | |
| 62' C. | 30 sec | } 10× |
| 68' C. | 5 min | |
| 93' C. | 15 sec | |
| 62' C. | 30 sec | } 17× |
| 68' C. | 5 min = 20 sec/cycle | |

For AR37 annealing temperatures of 60° C. and 58° C. were also tried.

Results

Approximate products based on gel ladder:

| | |
|---|---|
| AR1 | ~2.8 Kb |
| AR37 | ~1.8 Kb |
| AR42 | ~1.8 Kb |
| AR542 | ~2.2 Kb |
| AR584 | ~2.2 Kb |
| AR601 | ~2.8 Kb |

-continued

| | |
|---|---|
| FL1 | ~2.8 Kb |
| E. ciliarus | ~1.6 Kb |

PCR products were gel purified and sequenced to provide IGS sequences for subsequent alignment between strains. The sequences of the amplified IGS sequences are shown in SEQ ID NO: 9 to 16.

Example 2

PCR Primer Design and Optimisation of PCR Methodology and Conditions to Distinguish Between Endophyte Strains Materials and Methods IGS sequences were aligned using clustalW as shown in FIG. 3.

Primers that flanked regions unique to specific endophyte strains were designed (Table 1)

Results

The primer pairs listed in Table 1 were designed to IGS sequences and trialled by High Resolution Melting (HRM) PCR to select those useful for providing distinct High Resolution Melting (HRM) profiles for the three endophyte strains (wild type, AR1 and AR37).

TABLE 1

| Primer | Sequence | SEQ ID NO: |
|---|---|---|
| DH008F | gaagagttactagctgatgc | 1 |
| AR1F | gaagagttactagctgatg | 2 |
| endoph_F1 | tagctgatgcgctgttgttc | 3 |
| DH004F | ctcatgtgcgggcagtgtag | 4 |
| DH004R | ctacactgcccgcacatgag | 5 |
| DH_IGS_F | cctaacctatacctgcccg | 6 |
| AR1R | cgcgggcaggtataggtt | 7 |
| DH007R | cctacatataatagcattgc | 8 |

The expected amplicon, the number of Single Nucleotide Polymorphisms (SNPs) and the presence of deletions within a particular strain IGS sequence is also listed in Table 2 below, for the primer pairs shown.

TABLE 2

| Primer pair | Endophyte | Size | SNP's | Deletions (BP) |
|---|---|---|---|---|
| DH008F/DH004R | AR1 | 145 | 5 | 21 |
| | AR37 | 145 | | 21 |
| | WT | 166 | | |
| DH008F/AR1R | AR1 | 174 | 5 | 21 |
| | AR37 | 174 | | 21 |
| | WT | 195 | | |
| AR1F/DH004R | AR1 | 145 | 5 | 21 |
| | AR37 | 145 | | 21 |
| | WT | 166 | | |
| AR1F/AR1R | AR1 | 174 | 5 | 21 |
| | AR37 | 174 | | 21 |
| | WT | 195 | | |
| endoph_F1/DH004R | AR1 | 135 | 3 | 21 |
| | AR37 | 135 | | 21 |
| | WT | 156 | | |

TABLE 2-continued

| Primer pair | Endophyte | Size | SNP's | Deletions (BP) |
|---|---|---|---|---|
| endoph_F1/AR1R | AR1 | 164 | 3 | 21 |
| | AR37 | 164 | | 21 |
| | WT | 185 | | |
| DH004F/DH007R | AR1 | 336 | | 24 |
| | AR37 | 275 | 10 | 40, 24 & 21 |
| | WT | 360 | | |
| DH_IGSF/DH007R | AR1 | 307 | 10 | 24 |
| | AR37 | 246 | | 40, 24 & 21 |
| | WT | 331 | | |
| | AR1 | 461 | | 21 & 24 |
| | AR37 | 400 | 15 | 21, 40, 24 & 21 |
| | WT | 506 | | |
| B11F/B11R | AR1 | 148 | N/A | N/A |
| | AR37 | 130 | N/A | N/A |
| | ctWT | 177 | N/A | N/A |
| | AR42 | 181 | N/A | N/A |

Control DNA extracted from endophyte grown in culture was used to perform HRM on the primer pairs listed in Table 2.

Primer pair DH008F/DH007R was found to give distinct HRM profiles as shown in FIG. 1.

PCR conditions for primer pair DH008F/DH007R were:

94° C. 4 min,
94° C. 30 sec, 55'C 30 sec, 72'C 45 sec×40
72° C. 7 min

Used amplitaq Gold Polymerase
25 ng genomic DNA
10×PCR Buffer gold 1.5 ul/15 ul reaction
50 mM MgCl2 0.45 ul
25 mM dNTP's 0.12 ul
10 uM DH008F/DH007R 0.75 ul
5 U/ul Ampli Taq Gold 0.12 ul
MQ 9.06 ul Note that the endophytes are distinguished based on a melting profile rather than on a peak size basis.

Example 3

Optimising Seedling Germination/Growth Conditions from Maximum Hyphal Biomass in Young Leaves Materials and Methods Optimisation was performed on ryegrass cultivar Samson infected with the endophyte AR1. (Accession number A10735). A sample of the seeds was heat treated to simulate non-viable endophyte-infected seed. Endophyte viability tests were conducted by Western blotting tillers squashed onto nitrocellulose membrane using standard techniques. The Blotting tests were conducted to determine the % viability of AR1-infected seed in the accession for comparison with PCR results, and to confirm that the endophyte in the heat-treated seed was non-viable. The seed of this accession contained 95% viable endophyte and confirmed that all endophytes in the heat-treated seed were non-viable (FIG. 5).

To determine the impact of temperature on fungal biomass in planta, seeds were germinated for 13 days at 19, 22, and 28° C. and seedlings were assessed for endophyte infection by PCR using primers designed to 18S rRNA gene.

RJ240F/18S rRNA (*E. festucae*):
(SEQ ID NO: 19)
ATCTCTTGGTTCTGGCATCG

RJ240R/18S rRNA (*E. festucae*):
(SEQ ID NO: 20)
TGGTTGCGAGGTGGTATGTT

Results

PCR analysis on seedlings demonstrated by blotting to have >95% viability showed that no PCR products were obtained for seeds germinated at either 19 or 28° C. On the contrary all seedlings tested from the 22° C. germinated seeds amplified PCR products of the expected size. The results demonstrate that endophyte biomass in planta is insufficient in seedlings grown either at lower (19° C.) or higher (28° C.) temperatures. On the basis of this result all future DNA extractions and subsequent PCRs (either genotyping or HRM) were performed on seedlings grown at 22° C.

Example 4

Assessing Percentage of Beneficial and Non-Beneficial Endophyte in Seed Batches

Materials and Methods

Fresh seed was provided and sown into compost as described above. After 14 days growth at 22° C. the first leaf of 92 seedlings were harvested into a 96 well robotics microtitre tray. The remaining 4 wells comprised control DNA to assess endophyte type (wt, AR1, AR37) and PCR conditions.

DNA was extracted robotically by Slipstream Automation and transferred robotically into a 96 well HRM plate. HRM PCR was performed using primers DH008F/DH007R and the conditions described above. The HRM software determines the high resolution melting profile for each well and automatically assigns a viability status (product detected) and endophyte type (AR1, AR37 or wt). The percent viability and percent off type is a straight forward calculation of the number of positives out of 92 multiplied by 100.

Initial proof of concept experiments retained the original seedlings from which the first leaf was harvested and seedlings were grown for a further 4 weeks (6 weeks total) and then immuno blotted to determine their infection status by an independent (non-molecular) method. Blotting results were compared to the results obtained for HRM with the same seedlings.

Additionally seed lines comprising different ryegrass cultivars and different endophyte strains were provided by GTL for assessment by HRM and these were also compared to blotting results (Table 2)

Results

There was a high correlation between the blotting results and the HRM results, as shown in Table 3 below.

TABLE 3

| Line No | Endophyte | Cultivar | Seedling Age (days) | AgResearch Extracted DNA | | | | Slipstream Automation Extracted DNA | | | | SSA HRM Results | |
|---|---|---|---|---|---|---|---|---|---|---|---|---|---|
| | | | | HRM Results | | Blotted Results | | HRM Results | | Blotted Results | | | |
| | | | | Actual | % | blotted | % | Actual | % | blotted | % | Actual | % |
| A16360 | AR1 | 5773 AR1 | 10 | 87/91 | 96% | 89/91 | 98% | 74/90 | 82% | 90/90 | 100% | 88/91 | 97% |
| | | | 12 | 88/90 | 98% | 88/90 | 98% | 87/81 | 96% | 90/91 | 99% | | |
| | | | 14 | 89/92 | 97% | 91/92 | 99% | 86/87 | 99% | 87/87 | 100% | | |
| A15403 | AR37 | Samson AR37 | 10 | 83/92 | 90% | 85/92 | 92% | 55/89 | 62% | 81/89 | 91% | 77/90 | 86% |
| | | | 12 | 84/91 | 92% | 83/91 | 91% | 74/90 | 82% | 81/90 | 90% | | |
| | | | 14 | 76/89 | 85% | 76/89 | 85% | 80/92 | 87% | 81/92 | 88% | | |
| A15862 | AR37 | Commando AR37 | 10 | 69/92 | 75% | 70/92 | 76% | 66/91 | 73% | 79/91 | 87% | 68/88 | 77% |
| | | | 12 | 85/92 | 92% | 84/92 | 91% | 72/88 | 82% | 73/88 | 83% | | |
| | | | 14 | 79/91 | 87% | 79/91 | 87% | 72/91 | 79% | 73/91 | 80% | | |
| N1892 | AR1 | Marsden AR1 | 10 | 80/84 | 95% | 82/84 | 98% | 62/89 | 70% | 84/89 | 94% | 85/91 | 93% |
| | | | 12 | 84/90 | 93% | 88/90 | 98% | 84/91 | 92% | 89/91 | 98% | | |
| | | | 14 | 86/91 | 95% | 88/91 | 97% | 86/92 | 93% | 89/92 | 97% | | |

REFERENCES

Fletcher, L. R. 1999: "Non-toxic" endophytes in ryegrass and their effect on livestock health and production. In Ryegrass endophyte: an essential New Zealand symbiosis.

Fletcher, L. R.; Easton, H. S. 2000: Using Endophytes for Pasture Improvement in New Zealand. In Proceedings of The Grassland Conference 2000, 4th International *Neotyphodium*/Grass Interactions Symposium. Eds. Paul, V. H.; Dapprich, P. D. Universtat, Paderborn, pp 149-162.

Leuchtmann, A. 1997: Ecological diversity in *Neotyphodium*-infected grasses as influenced by host and fungus characteristics. In *Neotyphodium*/Grass Interactions, Eds. Bacon, C. W.; Hill, N. S. Plenum Press, New York, pp 93-108.

Mullis et al., Eds. 1994 The Polymerase Chain Reaction, Birkhauser

Newton C R, Graham A, Heptinstall L E, Powell S J, Summers C, Kalsheker N, Smith J C, and Markham A F (1989). "Analysis of any point mutation in DNA. The amplification refractory mutation system (ARMS)". Nucleic Acids Research 17 (7): 2503-2516.

Rowan, D D.; Latch, G. C. M. 1994: Utilization of endophyte-infected perennial ryegrasses for increased insect resistance. In Biotechnology of endophyte fungi in grasses. Eds. Bacon, C. W. White, J. CRC Press, pp 169-183.

Stuedemann, J. A.; Hoveland. C. 1988: Fescue endophyte: History and impact on animal agriculture. Journal of Production Agriculture 1: 39-44.

Zietkiewicz E., Rafalski A., and Labuda D. (1994). "Genome fingerprinting by simple sequence repeat (SSR)-anchored polymerase chain reaction amplification". Genomics 20 (2): 176-83.

SUMMARY OF SEQUENCES

| SEQ ID NO | Sequence | Type | Reference |
|---|---|---|---|
| 1 | Polynucleotide | Artificial, primer | DH008F |
| 2 | Polynucleotide | Artificial, primer | AR1F |
| 3 | Polynucleotide | Artificial, primer | endoph_Fl |
| 4 | Polynucleotide | Artificial, primer | DH004F |
| 5 | Polynucleotide | Artificial, primer | DH004R |
| 6 | Polynucleotide | Artificial, primer | DH_IGS_F |
| 7 | Polynucleotide | Artificial, primer | AR1R |
| 8 | Polynucleotide | Artificial, primer | DH007R |
| 9 | Polynucleotide | Endophyte IGS region | ctWT |
| 10 | Polynucleotide | Endophyte IGS region | AR42 |
| 11 | Polynucleotide | Endophyte IGS region | AR37 |
| 12 | Polynucleotide | Endophyte IGS region | AR1 |
| 13 | Polynucleotide | Endophyte IGS region | AR601 |
| 14 | Polynucleotide | Endophyte IGS region | AR584 |
| 15 | Polynucleotide | Endophyte IGS region | AR542 |
| 16 | Polynucleotide | Endophyte IGS region | AR1501 [FL1] |
| 17 | Polynucleotide | Artificial, primer | RJ243F (IGSF, LR12R |
| 18 | Polynucleotide | Artificial, primer | RJ243R (IGSR, invSRIR) |
| 19 | Polynucleotide | 18S rRNA Primer | RJ240F |
| 20 | Polynucleotide | 18S rRNA Primer | RJ240R |

The invention claimed is:

1. A method for detecting the presence of viable fungal endophyte in a plant, the method comprising detecting the presence of a fungal endophyte in a young leaf or extract thereof, from the plant, wherein detecting the presence of the fungal endophyte in the young leaf or extract is indicative of the presence of viable fungal endophyte in the plant, wherein the endophyte is detected by a method that identifies the presence of a particular species or strain of endophyte, wherein at least one primer that hybridizes to a species-specific or strain-specific part of the intergenic region (IGS) of the ribosomal repeat region of a fungal endophyte is used in a PCR-based method to detect the presence of the endophyte, and wherein the fungal endophyte is from the genus *Neotyphodium*.

2. The method of claim 1 in which the young leaf is one of the first 5 leaves produced by the plant after germination of a seed of the plant.

3. The method of claim 1 in which the young leaf is the first leaf produced by the plant after germination of a seed of the plant.

4. The method of claim 1 in which the young leaf is a leaf from a seedling of the plant that is produced within 4 weeks after germination of a seed of the plant.

5. The method of claim 1 in which the young leaf is from a seedling of the plant that is produced less than 14 days after germination of a seed of the plant.

6. The method of claim 1 in which the young leaf is from a seedling that has grown sufficiently for the leaf to have separated from the coleoptile.

7. The method of claim 1 in which the young leaf is excised, to substantially separate it from other tissues or organs of the plant, before use in the method.

8. The method of claim 1 in which the young leaf is excised, to substantially separate it from the coleoptile, as well as from other tissues or organs, of the plant, before use in the method.

9. The method of claim 1 in which the young leaf is excised, to substantially separate it from the coleoptile and any attached seed, as well as from other tissues or organs, of the plant, before use in the method.

10. The method of claim 1 in which the PCR-based method is quantitative PCR or real time PCR.

11. The method of claim 1 in which the PCR-based method is High Resolution Melting (HRM) real time PCR.

12. The method of claim 1 in which PCR is performed using primers that hybridise to nucleic acid in the endophyte.

13. The method of claim 1 in which at least one primer used in the PCR-based method, is specific for the strain detected, and presence or absence of an amplification product is indicative of presence or absence of the endophyte.

14. The method of claim 1 in which detection is specific for the species or strain detected and in which specificity is determined by the size of the amplified product.

15. The method of claim 1 in which detection is specific for the species or strain detected and in which specificity is determined by the kinetics of production of amplified product.

16. The method of claim 15 in which specificity is determined by the melting profile of the amplified product.

17. The method of claim 16 in which different melting profiles are produced in different species and strains, as a result of differences in sequences to which the primer hybridizes, in different endophyte species or strains.

18. The method of claim 1 in which a seed of the plant is germinated under conditions to maximize hyphal biomass in the young leaves, before the plant is used in the method.

19. The method of claim 1 in which the seed is germinated under conditions to maximize hyphal biomass in the seed in the first emerging leaf, before the plant is used in the method.

20. The method of claim 18 in which the seed is germinated in the temperature range 18 to 26° C.

21. The method of claim 18 in which the seed is germinated at about 22° C.

22. The method of claim 18 in which the seed is germinated in a 16/8 hour light/dark regime.

23. The method of claim 18 in which the seed is germinated in a 12/12 hour light/dark regime.

24. The method of claim 1 in which presence of the endophyte is detected in an extract from the young leaf.

25. The method of claim 24 in which the method includes the step of preparing an extract from the young leaf.

26. The method of claim 1 in which the method includes the step of excising the young leaf.

27. The method of claim 1 which includes the steps of excising the young leaf and making an extract.

28. The method of claim 1 in which the method includes the steps of germinating the seed, and excising the young leaf.

29. The method of claim 1 in which the method includes the steps of germinating the seed, excising the young leaf, and making an extract.

30. The method of claim 1 which is used to screen batches of seed to assess which endophyte species, strain, or strains, is or are present in the batch.

31. The method of claim 30 in which a small sample of seeds is taken from the larger batch and the method is performed on a young leaf after germination of the seeds from the small sample.

32. The method of claim 31 in which the method is used to measure the proportion or percentage of seeds in the small sample that contain viable endophytes of a particular species or strain, in order to estimate the proportion or percentage of seeds in the large batch that contain the viable endophytes.

33. The method of claim 31 in which the method is used to measure the proportion or percentage of seeds in the small sample that contain viable contaminating endophytes, in order to estimate the proportion or percentage of seeds in the large batch that contain viable contaminating endophytes.

34. The method of claim 1 in which at least one step is automated.

35. The method of claim 1 in which the primer has at least 80% identity to any one of the sequences of SEQ ID NO:1 to SEQ ID NO:8.

36. The method of claim 1 in which the primer has the sequence of any one of SEQ ID NO:1 to SEQ ID NO:8.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: synthesised

<400> SEQUENCE: 1
gaagagttac tagctgatgc                                                    20

<210> SEQ ID NO 2
<211> LENGTH: 19
<212> TYPE: DNA
<213> ORGANISM: Artificial Sequence
<220> FEATURE:
<223> OTHER INFORMATION: synthesised

<400> SEQUENCE: 2
gaagagttac tagctgatg                                                     19

<210> SEQ ID NO 3
<211> LENGTH: 20
<212> TYPE: DNA
<213> ORGANISM: Artificial Sequence
<220> FEATURE:
<223> OTHER INFORMATION: synthesised

<400> SEQUENCE: 3
tagctgatgc gctgttgttc                                                    20

<210> SEQ ID NO 4
<211> LENGTH: 20
<212> TYPE: DNA
<213> ORGANISM: Artificial Sequence
<220> FEATURE:
<223> OTHER INFORMATION: synthesised

<400> SEQUENCE: 4
ctcatgtgcg ggcagtgtag                                                    20

<210> SEQ ID NO 5
<211> LENGTH: 20
<212> TYPE: DNA
<213> ORGANISM: Artificial Sequence
<220> FEATURE:
<223> OTHER INFORMATION: synthesised

<400> SEQUENCE: 5
```

```
ctacactgcc cgcacatgag                                              20
```

<210> SEQ ID NO 6
<211> LENGTH: 19
<212> TYPE: DNA
<213> ORGANISM: Artificial Sequence
<220> FEATURE:
<223> OTHER INFORMATION: synthesised

<400> SEQUENCE: 6

```
cctaacctat acctgcccg                                               19
```

<210> SEQ ID NO 7
<211> LENGTH: 18
<212> TYPE: DNA
<213> ORGANISM: Artificial Sequence
<220> FEATURE:
<223> OTHER INFORMATION: synthesised

<400> SEQUENCE: 7

```
cgcgggcagg tataggtt                                                18
```

<210> SEQ ID NO 8
<211> LENGTH: 20
<212> TYPE: DNA
<213> ORGANISM: Artificial Sequence
<220> FEATURE:
<223> OTHER INFORMATION: synthesised

<400> SEQUENCE: 8

```
cctacatata atagcattgc                                              20
```

<210> SEQ ID NO 9
<211> LENGTH: 506
<212> TYPE: DNA
<213> ORGANISM: Neotyphodium lolii
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (474)..(475)
<223> OTHER INFORMATION: n is a, c, g, or t

<400> SEQUENCE: 9

```
gaagagttac tagctgatgc nctnntgttc tctgtgtggg cgctgttgtt ctctgtgcgg   60
gcgctgttgt gctctgtgcg ggcgatggtt cctctgtgcg ggcgctgtcc ttgtgcgtgc  120
gtgcgatgtt gttgtgtacg ggcgcgctca tgtgcgggca gtgtaggtta ggcgcctaac  180
ctatacctgc ccgcgcacgc tgtggtgtg cgggcgatgg ttcctctgtg cgggcgctgt  240
ccttgtgcgt gcgggcgatg ttatgctctg tgtgggtgat gttatcctct gtgcgggcgc  300
tgttgtcctc tgtgggtgat gctgtcctct atgcaggcgc tgttgtcctc tgtgcgagcg  360
ctagtgttct ctatgtgggt gatgttatta ttctctatgc gggtgatgtt attctctgtg  420
cgagcgctat tattctccgt gtgggcgctg ttatcctcta tgtgggcgct gtgnntgtgc  480
gtgcgggcaa tgctattata tgtagg                                       506
```

<210> SEQ ID NO 10

```
<211> LENGTH: 506
<212> TYPE: DNA
<213> ORGANISM: Neotyphodium lolii

<400> SEQUENCE: 10
gaagagttac tagctgatgc gctgttgttc tctgtgtggg cgctgttgtt ctctgtgtgg      60
gcgctgttgt gctctgtgcg ggcgatggtt cctctgtgcg ggcgctgtcc ttgtgcgtgc     120
gtgcgatgtt gttgtgtacg ggcgcgctca tgtgcgggca gtgtaggtta ggcgcctaac    180
ctatacctgc ccgcgcacgc tgtgggtgtg cgggcgatgg ttcctctgtg cgggcgctgt     240
ccttgtgcgt gcgggcgatg ttatgctctg tgtgggtgat gttatcctct gtgcgggcgc     300
tgttgtcctc tgtgggtgat gctgtcctct atgcaggcgc tgttgtcctc tgtgcgagcg     360
ctagtgttct ctatgtgggt gatgttatta ttctctatgc gggtgatgtt attctctgtg     420
cgagcgctat tattctccgt gtgggcgctg ttatcctcta tgtgggcgct gtgggtgtgc     480
gtgcgggcaa tgctattata tgtagg                                          506

<210> SEQ ID NO 11
<211> LENGTH: 400
<212> TYPE: DNA
<213> ORGANISM: Neotyphodium lolii

<400> SEQUENCE: 11
gaagagttac tagctgatgc gatgttgtgc tctgtgcggg cgctgttgtg ctctgtgcgg      60
gcgatggttc ctttgtgcgg gcgctgtcct tgtgcgtgcg tgcgatgttg ttatgtacgg     120
gcgcgctcat gtgcgggcag tgtaggttag gcgcctaacc tatacctgcc cgcgcacgct    180
gtgggtgtgc gggcgatggt tcctctgtgc gggcgctgtc cttgtgcgtg cgggcgatgt     240
tatgctctgt gtgggtgatg ttatcctctg tgcgggcgct gtcgtcctct gtgcgagcgc     300
tattattctc cgtgtgggcg ctgtcgtcct ctgtgcgagc gctattattc ccgtgtgggc     360
cgctgtgggt gtgcgtgcgg gcaatgctat tatatgtagg                           400

<210> SEQ ID NO 12
<211> LENGTH: 461
<212> TYPE: DNA
<213> ORGANISM: Neotyphodium lolii

<400> SEQUENCE: 12
gaagagttac tagctgatgc gctgttgttc tctgtgtggg cgctgttgtg ctctgtgcgg      60
gcgatggttc ctctgtgcgg gcgctgtcct tgtgcgtgcg tgcgatgttg ttgtgtacgg     120
gcgcgctcat gtgcgggcag tgtaggttag gcgcctaacc tatacctgcc cgcgcacgct    180
gtgggtgtgc gggcgatggt tcctctgtgc gggcgctgtc cttgtgcgtg cgggcgatgt     240
tatgctctgt gtgggtgatg ttatcctctg tgcgggcgct gttgtcctct gtgggtgatg     300
ctgtcctcta tgcaggcgct gttgtcctct gtgcgagcgc tagtgttctc tatgcgggtg     360
atgttattct ctgtgcgagc gctattattc ccgtgtgggc gctgttatc ctctatgtgg     420 gcgctgtggg tgtgcgtgcg ggcaatgcta ttatatgtag g                         461

<210> SEQ ID NO 13
<211> LENGTH: 360
<212> TYPE: DNA
<213> ORGANISM: Neotyphodium coenophialum

<400> SEQUENCE: 13
gaagagttac tagctgatgc gatgttgtgc tctgtgcggg cgatggttcc tttgtgcggg      60
```

```
ccgctgtcct tgtgcgtgcg tgcgatgttg ttatgtacgg gcgcgctcat gtgcgggcag    120
tgtaggttag gcgcctaacc tatacctgcc cgcgcacgct gtgggtgtgc gggcgatggt    180
tcctctgtgc gggcgctgtc cttgtgcgtg cgggcgatgt tgtgatactc tgtgtgggtg    240
atgttatcct ctgtgcgggc gctgtcgtcc tctgtgggtg atgtcgtcct ctgtgcgagc    300
gctattattc tccgtgtggg cgctgtgggt gtgcgtgcgg gcaatgctat tatatgtagg    360
```

<210> SEQ ID NO 14
<211> LENGTH: 274
<212> TYPE: DNA
<213> ORGANISM: Neotyphodium coenophialum

<400> SEQUENCE: 14

```
gaagagttac tagctgatgc gatgttgtgc tctgtgcggg cgctgttgtg ctctgtgcgg     60
gcgatggttc ctttgtgcgg gcgctgtcct tgtgcgtgcg tgcgatgtcg ttatgtacgg    120
gcgcgctcat gtgcgggcag tgtaggttag gcgcctaacc tatacctgcc cgcgcacgct    180
gtgggtgtgc gggcgatggt tcctctgtgc gagcgctatt attctccgtg tgggcgctgt    240
gggtgtgcgt gcgggcaatg ctattatatg tagg                                274
```

<210> SEQ ID NO 15
<211> LENGTH: 274
<212> TYPE: DNA
<213> ORGANISM: Neotyphodium coenophialum

<400> SEQUENCE: 15

```
gaagagttac tagctgatgc gatgttgtgc tctgtgcggg cgctgttgtg ctctgtgcgg     60
gcgatggttc ctttgtgcgg gcgctgtcct tgtgcgtgcg tgcgatgtcg ttatgtacgg    120
gcgcgctcat gtgcgggcag tgtaggttag gcgcctaacc tatacctgcc cgcgcacgct    180
gtgggtgtgc gggcgatggt tcctctgtgc gagcgctatt attctccgtg tgggcgctgt    240
gggtgtgcgt gcgggcaatg ctattatatg tagg                                274
```

<210> SEQ ID NO 16
<211> LENGTH: 366
<212> TYPE: DNA
<213> ORGANISM: Epichloe festucae

<400> SEQUENCE: 16

```
gaagagttac tagctgatgc gctgttgtcc tctgtgcggg cgctgtcgtc cactgtgggt     60
gctgtcgtcc actgtgggtg atgttgtcct ctgtgtgggt gatgtcctcg tgcgtgcggg    120
cgctgttgtc ctccgtgcgg gcgatgttgt cctccgtgcg ggcgatgttg tcctccgtgc    180
gggcgatgtt gtcatgtgtg ggcgcgctca tgtgcgggca gtgtaggtta ggcgcctaac    240
ctatacctgc ccgcgcacgc tatgggtgtg cgcgctgtcg tcctctgtgc gggcgctgtc    300
gtcctctgtg cgggcgctgt cgtcctctgt gtgggtgtgc gtgcgggcaa tgctattata    360
tgtagg                                                               366
```

<210> SEQ ID NO 17
<211> LENGTH: 23
<212> TYPE: DNA
<213> ORGANISM: Artificial Sequence
<220> FEATURE:
<223> OTHER INFORMATION: synthesised

<400> SEQUENCE: 17

```
gaacgcctct aagtcagaaa tcc                                              23

<210> SEQ ID NO 18
<211> LENGTH: 21
<212> TYPE: DNA
<213> ORGANISM: Artificial Sequence
<220> FEATURE:
<223> OTHER INFORMATION: synthesised

<400> SEQUENCE: 18
actggcagaa tcaaccaggt a                                                21

<210> SEQ ID NO 19
<211> LENGTH: 20
<212> TYPE: DNA
<213> ORGANISM: Artificial Sequence
<220> FEATURE:
<223> OTHER INFORMATION: synthesised

<400> SEQUENCE: 19
atctcttggt tctggcatcg                                                  20

<210> SEQ ID NO 20
<211> LENGTH: 20
<212> TYPE: DNA
<213> ORGANISM: Artificial Sequence
<220> FEATURE:
<223> OTHER INFORMATION: synthesised

<400> SEQUENCE: 20
tggttgcgag gtggtatgtt                                                  20
```